(12) United States Patent  (10) Patent No.: US 7,960,422 B2
Arzel et al.  (45) Date of Patent: Jun. 14, 2011

(54) PHARMACEUTICALLY ACTIVE COMPOUNDS CONTAINING TETRAZOLYL AND TRIAZOLYL RINGS

(75) Inventors: Erwan Arzel, Södertälje (SE); Louise Edwards, Ontario (CA); Methvin Isaac, Ontario (CA); Donald A. McLeod, Sandy, UT (US); Abdelmalik Slassi, Ontario (CA); Tao Xin, Ontario (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/285,988

(22) Filed: Oct. 17, 2008

(65) Prior Publication Data
US 2009/0131454 A1 May 21, 2009

Related U.S. Application Data

(60) Provisional application No. 60/981,294, filed on Oct. 19, 2007.

(51) Int. Cl.
*A61K 31/41* (2006.01)
(52) U.S. Cl. .................... 514/381; 546/272.4; 548/252; 548/264.2
(58) Field of Classification Search .................. 514/381; 546/272.4; 548/252, 264.2
See application file for complete search history.

(56) References Cited

U.S. PATENT DOCUMENTS
4,663,332 A  5/1987  Carson et al.

FOREIGN PATENT DOCUMENTS
| WO | WO-93-02677 A1 | 2/1993 |
| WO | WO-01-85705 A1 | 11/2001 |
| WO | WO-03-002559 A2 | 1/2003 |
| WO | WO-03-020721 A1 | 3/2003 |
| WO | WO-03/029210 A2 | 4/2003 |
| WO | WO-03/077918 A | 9/2003 |
| WO | WO-2004/014881 A2 | 2/2004 |
| WO | WO-2005/077345 A1 | 8/2005 |
| WO | WO-2005/080356 A1 | 9/2005 |
| WO | WO-2005/080379 A1 | 9/2005 |
| WO | WO-2005/080386 A1 | 9/2005 |
| WO | WO-2006/014185 A1 | 2/2006 |
| WO | WO-2007/040982 A1 | 4/2007 |
| WO | WO-2007/130820 A2 | 11/2007 |
| WO | WO-2007/130823 A2 | 11/2007 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
STN International; file CAPLUS; AN:2003:396864 (WO 03042188 A1).
Schoepp et al., Trends Pharmacol. Sci. 14:13 (1993).
Schoepp, Neurochem. Int. 24:439 (1994).
Pin et al., Neuropharmacology 34:1 (1995).
Bordi and Ugolini, Prog. Neurobiol. 59:55 (1999).
Nakanishi, Neuron 13:1031 (1994).
Knopfel et al., J. Med. Chem. 38:1417 (1995).
Pin et al., PNAS 89:10331 (1992).
Minakami et al., BBRC 199:1136 (1994).
Joly et al., J. Neurosci. 15:3970 (1995).
Baskys, Trends Pharmacol. Sci. 15:92 (1992).
Watkins et al., Trends Pharmacol. Sci. 15:33 (1994).
Bashir et al., Nature 363:347 (1993).
Bortolotto et al., Nature 368:740 (1994).
Aiba et al., Cell 79:365 (1994).
Aiba et al., Cell 79:377 (1994).
Meller et al., Neuroreport 4:879 (1993).
Bordi and Ugolini, Brain Res. 871:223 (2000).
Cunningham et al., Life Sci. 54:135 (1994).
Hollman et al., Ann. Rev. Neurosci. 17:31 (1994).
Spooren et al., Trends Pharmacol. Sci. 22:331 (2001).
Gasparini et al. *Curr. Opin. Pharmacol.* 2:43 (2002).
Neugebauer *Pain* 98:1 (2002).
Holloway & Dent (1990) Gastroenterol. Clin. N. Amer. 19, pp. 517-535.
Janet Hoogstraate, PhD "Pharmacokinetic screening following single intravenous and oral dosing in rats", Research DMPK, AstraZeneca R&D Sodertalje Mar. 15, 2006.
Opposition, Costa Rica Patent Application No. 11.376, dated Oct. 26, 2010.

* cited by examiner

*Primary Examiner* — James O Wilson
*Assistant Examiner* — Douglas M Willis
(74) *Attorney, Agent, or Firm* — Connolly Bove Lodge & Hutz LLP

(57) ABSTRACT

Compounds of formula (I)

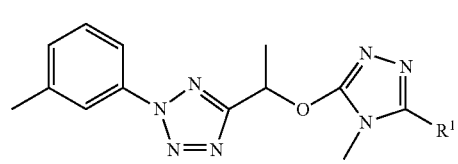

wherein R¹ is

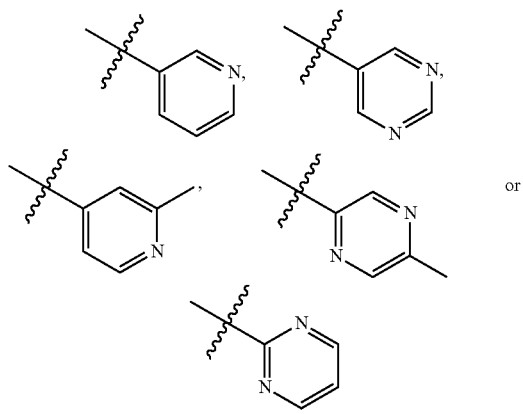

as well as pharmaceutically acceptable salts, hydrates and/or enantiomers thereof are useful as compounds that exhibit activity at metabotropic glutamate receptors.

2 Claims, No Drawings

PHARMACEUTICALLY ACTIVE COMPOUNDS CONTAINING TETRAZOLYL AND TRIAZOLYL RINGS

FIELD OF THE INVENTION

The present invention is directed to novel compounds, their use in therapy and pharmaceutical compositions comprising said novel compounds.

BACKGROUND OF THE INVENTION

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., Trends Pharmacol. Sci. 14:13 (1993), Schoepp, Neurochem. Int. 24:439 (1994), Pin et al., Neuropharmacology 34:1 (1995), Bordi and Ugolini, Prog. Neurobiol. 59:55 (1999).

Molecular cloning has identified eight distinct mGluR subtypes, termed mGluR1 through mGluR8. Nakanishi, Neuron 13:1031 (1994), Pin et al., Neuropharmacology 34:1 (1995), Knopfel et al., J. Med. Chem. 38:1417 (1995). Further receptor diversity occurs via expression of alternatively spliced forms of certain mGluR subtypes. Pin et al., PNAS 89:10331 (1992), Minakami et al., BBRC 199:1136 (1994), Joly et al., J. Neurosci. 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Neurological, Psychiatric and Pain Disorders

Attempts at elucidating the physiological roles of Group I mGluRs suggest that activation of these receptors elicits neuronal excitation. Various studies have demonstrated that Group I mGluRs agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, Trends Pharmacol. Sci. 15:92 (1992), Schoepp, Neurochem. Int. 24:439 (1994), Pin et al., Neuropharmacology 34:1 (1995), Watkins et al., Trends Pharmacol. Sci. 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., Nature 363:347 (1993), Bortolotto et al., Nature 368:740 (1994), Aiba et al., Cell 79:365 (1994), Aiba et al., Cell 79:377 (1994). A role for mGluR activation in nociception and analgesia also has been demonstrated, Meller et al., Neuroreport 4: 879 (1993), Bordi and Ugolini, Brain Res. 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, Neuron 13: 1031 (1994), Pin et al., Neuropharmacology 34:1, Knopfel et al., J. Med. Chem. 38:1417 (1995).

Further, Group I metabotropic glutamate receptors and mGluR5 in particular, have been suggested to play roles in a variety of pathophysiological processes and disorders affecting the CNS. These include stroke, head trauma, anoxic and ischemic injuries, hypoglycemia, epilepsy, neurodegenerative disorders such as Alzheimer's disease and pain. Schoepp et al., Trends Pharmacol. Sci. 14:13 (1993), Cunningham et al., Life Sci. 54:135 (1994), Hollman et al., Ann. Rev. Neurosci. 17:31 (1994), Pin et al., Neuropharmacology 34:1 (1995), Knopfel et al., J. Med. Chem. 38:1417 (1995), Spooren et al., Trends Pharmacol. Sci. 22:331 (2001), Gasparini et al. Curr. Opin. Pharmacol. 2:43 (2002), Neugebauer Pain 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics or anticonvulsants.

Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders.

Gastrointestinal Disorders

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, e.g. Holloway & Dent (1990) Gastroenterol. Clin. N. Amer. 19, pp. 517-535, has shown that most reflux episodes occur during transient lower esophageal sphincter relaxations (TLESRs), i.e. relaxations not triggered by swallows. It has also been shown that gastric acid secretion usually is normal in patients with GERD.

The novel compounds according to the present invention are assumed to be useful for the inhibition of transient lower esophageal sphincter relaxations (TLESRs) and thus for treatment of gastro-esophageal reflux disorder (GERD).

Because of their physiological and pathophysiological significance, there is a need for new potent mGluR agonists and antagonists that display a high selectivity for mGluR subtypes, particularly the Group I receptor subtype, most particularly the mGluR5. There is also a need for mGluR5 antagonists that do not lead to reactive metabolites and that have limited hERG interaction.

The object of the present invention is to provide compounds exhibiting an activity at metabotropic glutamate receptors (mGluRs), especially at the mGluR5 receptor.

DESCRIPTION OF THE INVENTION

The present invention is directed to a compound of formula I:

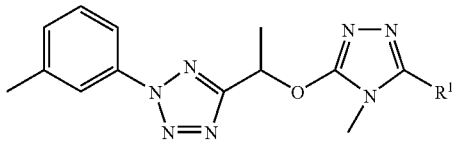

(I)

wherein $R^1$ is

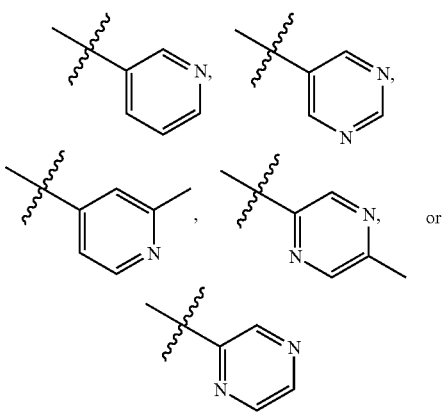

as well as pharmaceutically acceptable salts, hydrates, isoforms and/or enantiomers thereof. In one embodiment, the compound of formula I is the R-enantiomer. In another embodiment, the compound of formula I is the S-enantiomer.

Another embodiment is a pharmaceutical composition comprising as active ingredient a therapeutically effective amount of the compound according to formula I, in association with one or more pharmaceutically acceptable diluents, excipients and/or inert carriers.

Other embodiments, as described in more detail below, relate to a compound according to formula I for use in therapy, in treatment of mGluR5 mediated disorders, in the manufacture of a medicament for the treatment of mGluR5 mediated disorders.

Still other embodiments relate to a method of treatment of mGluR5 mediated disorders, comprising administering to a mammal a therapeutically effective amount of the compound according to formula I.

In another embodiment, there is provided a method for inhibiting activation of mGluR5 receptors, comprising treating a cell containing said receptor with an effective amount of the compound according to formula I.

The compounds of the present invention are useful in therapy, in particular for the treatment of neurological, psychiatric, pain, and gastrointestinal disorders.

It will also be understood by those of skill in the art that certain compounds of the present invention may exist in solvated, for example hydrated, as well as unsolvated forms. It will further be understood that the present invention encompasses all such solvated forms of the compounds of formula I.

Within the scope of the invention are also salts of the compounds of formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a salt with a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Additionally, quaternary ammonium salts can be prepared by the addition of alkylating agents, for example, to neutral amines.

In one embodiment of the present invention, the compound of formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

In further embodiments of the present invention, the compound of formula I may be converted to a pharmaceutically acceptable salt or solvate thereof with sulfonic acid, 1,2-ethanedisulfonic acid (both as 1:1 and 2:1), ethanesulfonic acid, nitric acid, 2-mesitylenesulfonic acid, 1,5-naphthalenedisulfonic acid (both as 1:1 and 2:1) or p-xylenesulfonic acid.

Pharmaceutical Composition

The compounds of the present invention may be formulated into conventional pharmaceutical compositions comprising a compound of formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, or from about 0.10% w to 50% w, of a compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

The compounds according to the present invention are useful in the treatment of conditions associated with excitatory activation of mGluR5 and for inhibiting neuronal damage caused by excitatory activation of mGluR5. The compounds may be used to produce an inhibitory effect of mGluR5 in mammals, including man.

The Group I mGluR receptors including mGluR5 are highly expressed in the central and peripheral nervous system and in other tissues. Thus, it is expected that the compounds of the invention are well suited for the treatment of mGluR5-mediated disorders such as acute and chronic neurological and psychiatric disorders, gastrointestinal disorders, and chronic and acute pain disorders.

The invention relates to compounds of Formula I, as defined hereinbefore, for use in therapy.

The invention relates to compounds of Formula I, as defined hereinbefore, for use in treatment of mGluR5-mediated disorders.

The invention relates to compounds of Formula I, as defined hereinbefore, for use in treatment of Alzheimer's disease senile dementia, AIDS-induced dementia, Parkinson's disease, amylotropic lateral sclerosis, Huntington's Chorea, migraine, epilepsy, schizophrenia, depression, anxiety, acute anxiety, opthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, Fragile X, autism, mental retardation, schizophrenia and Down's Syndrome.

The invention relates to compounds of Formula I, as defined above, for use in treatment of pain related to migraine, inflammatory pain, neuropathic pain disorders such as diabetic neuropathies, arthritis and rheumatiod diseases, low back pain, post-operative pain and pain associated with various conditions including cancer, angina, renal or billiary colic, menstruation, migraine and gout.

The invention relates to compounds of Formula I as defined hereinbefore, for use in treatment of stroke, head trauma, anoxic and ischemic injuries, hypoglycemia, cardiovascular diseases and epilepsy.

The present invention relates also to the use of a compound of Formula I as defined hereinbefore, in the manufacture of a medicament for the treatment of mGluR Group I receptor-mediated disorders and any disorder listed above.

One embodiment of the invention relates to the use of a compound according to Formula I in the treatment of gastrointestinal disorders.

Another embodiment of the invention relates a compound of formula I for the inhibition of transient lower esophageal sphincter relaxations, for the treatment of GERD, for the prevention of gastroesophageal reflux, for the treatment regurgitation, for treatment of asthma, for treatment of laryngitis, for treatment of lung disease, for the management of failure to thrive, for the treatment of irritable bowel syndrome (IBS) and for the treatment of functional dyspepsia (FD).

Another embodiment of the invention relates to the use of a compound of formula I for the manufacture of a medicament for inhibition of transient lower esophageal sphincter relaxations, for the treatment of GERD, for the prevention of gastroesophageal reflux, for the treatment regurgitation, for treatment of asthma, for treatment of laryngitis, for treatment of lung disease, for the management of failure to thrive, for the treatment of irritable bowel syndrome (IBS) and for the treatment of functional dyspepsia (FD).

Another embodiment of the present invention relates to the use of a compound of Formula I for treatment of overactive bladder or urinary incontinence.

The wording "TLESR", transient lower esophageal sphincter relaxations, is herein defined in accordance with Mittal, R. K, Holloway, R. H., Penagini, R., Blackshaw, L. A., Dent, J, 1995; *Transient lower esophageal sphincter relaxation. Gastroenterology* 109, pp. 601-610.

The wording "reflux" is herein defined as fluid from the stomach being able to pass into the esophagus, since the mechanical barrier is temporarily lost at such times.

The wording "GERD", gastro-esophageal reflux disease, is herein defined in accordance with van Heerwarden, M. A., Smout A. J. P. M, 2000, *Diagnosis of reflux disease. Baillière's Clin. Gastroenterol.* 14, pp. 759-774.

A further embodiment of the invention relates to the use of a compound according to Formula I for the manufacture of a medicament for the treatment of cough. In one embodiment, the cough to be treated is chronic cough. In a further embodiment, the cough to be treated is acute cough. The term chronic cough is defined in accordance with Kardos P et al (The German Respiratory Society's Guideline for the Diagnosis and Treatment of Patients with Acute and Chronic Cough Medizinische Klinik 2004; 99(8):468-75) as a cough that lasts longer than 8 weeks. However, chronic cough can also be defined as a cough lasting longer than 3 weeks or as a cough lasting longer than 2 months. The term "acute cough" is also defined in accordance with the reference above as a cough lasting less than 8 weeks.

The compounds of formula I above are useful for the treatment or prevention of obesity or overweight, (e.g., promotion of weight loss and maintenance of weight loss), prevention or reversal of weight gain (e.g., rebound, medication-induced or subsequent to cessation of smoking), for modulation of appetite and/or satiety, eating disorders (e.g. binge eating, anorexia, bulimia and compulsive) and cravings (for drugs, tobacco, alcohol, any appetizing macronutrients or non-essential food items).

The invention also provides a method of treatment of mGluR5-mediated disorders and any disorder listed above, in a patient suffering from, or at risk of, said condition, which comprises administering to the patient an effective amount of a compound of Formula I, as hereinbefore defined.

The dose required for the therapeutic or preventive treatment of a particular disorder will necessarily be varied depending on the host treated, the route of administration and the severity of the illness being treated.

In the context of the present specification, the term "therapy" and "treatment" includes prevention or prophylaxis, unless there are specific indications to the contrary. The terms "therapeutic" and "therapeutically" should be construed accordingly.

In this specification, unless stated otherwise, the term "antagonist" and "inhibitor" shall mean a compound that by any means, partly or completely, blocks the transduction pathway leading to the production of a response by the ligand.

The term "disorder", unless stated otherwise, means any condition and disease associated with metabotropic glutamate receptor activity.

Non-Medical Use

In addition to their use in therapeutic medicine, the compounds of Formula I, as well as salts and hydrates of such compounds, are useful as pharmacological tools in the development and standardisation of in vitro and in vivo test systems for the evaluation of the effects of inhibitors of mGluR related activity in laboratory animals such as cats, dogs, rabbits, monkeys, rats and mice, as part of the search for new therapeutic agents.

Methods of Preparation

Synthesis of Intermediates

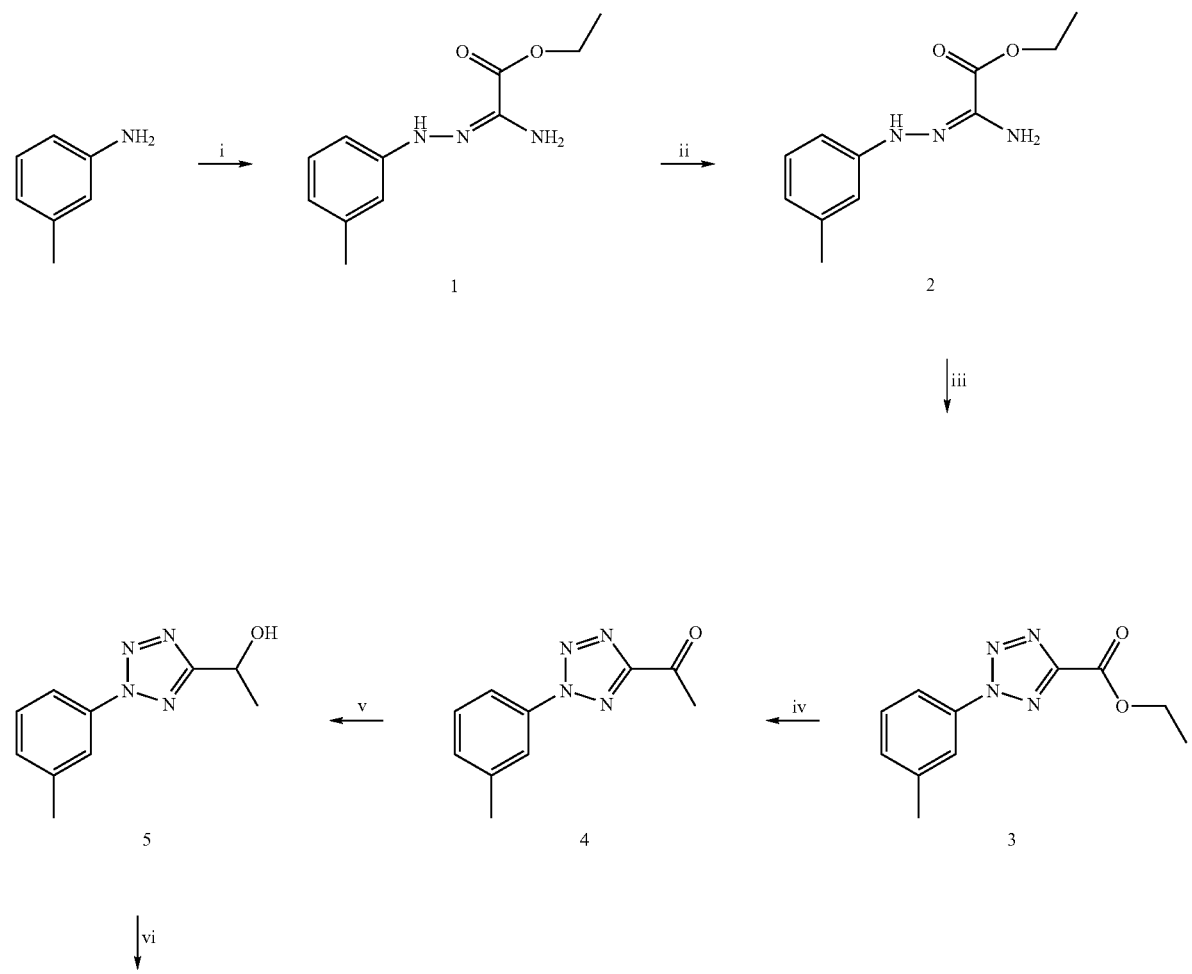

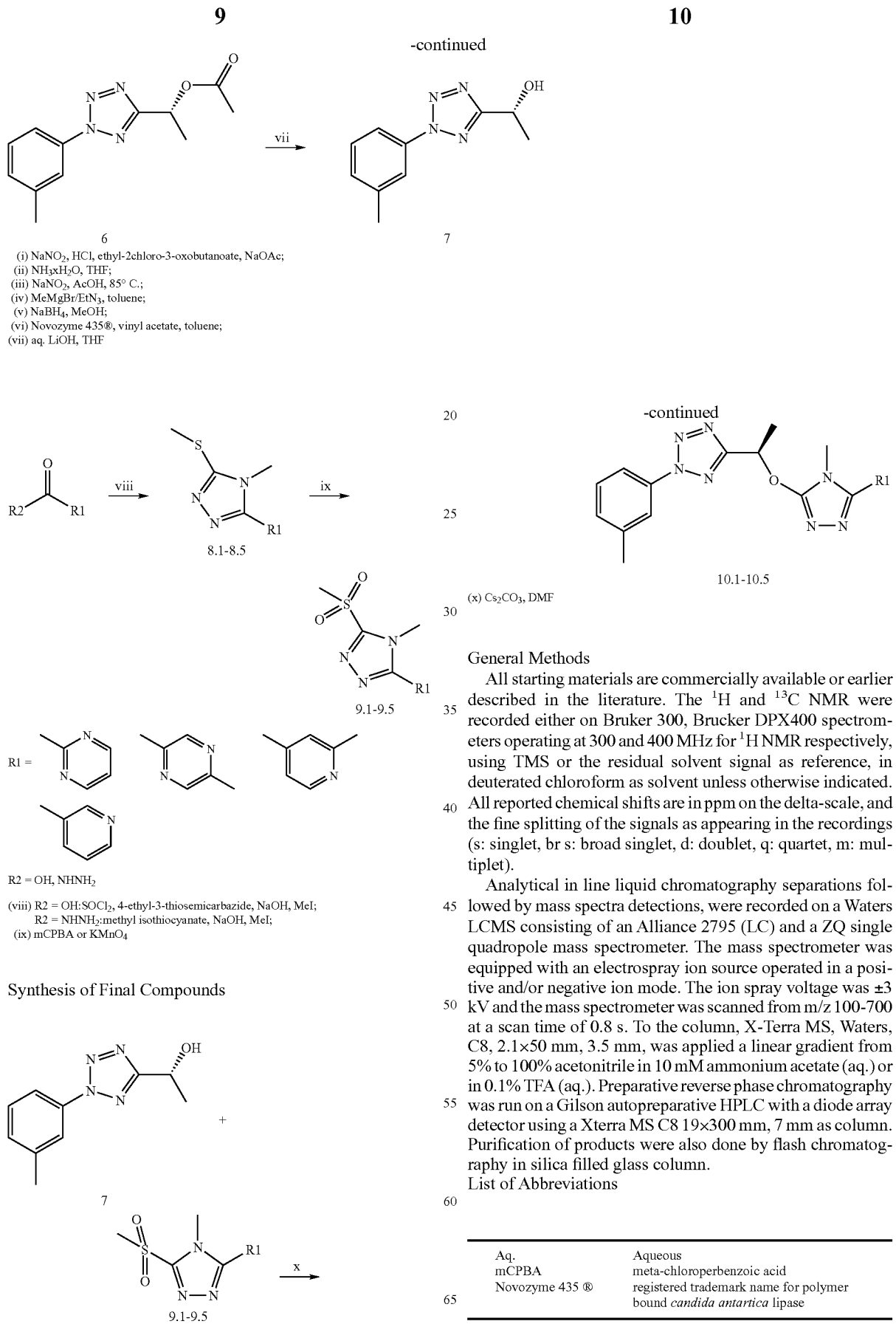

General Methods

All starting materials are commercially available or earlier described in the literature. The $^1$H and $^{13}$C NMR were recorded either on Bruker 300, Brucker DPX400 spectrometers operating at 300 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, q: quartet, m: multiplet).

Analytical in line liquid chromatography separations followed by mass spectra detections, were recorded on a Waters LCMS consisting of an Alliance 2795 (LC) and a ZQ single quadropole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.) or in 0.1% TFA (aq.). Preparative reverse phase chromatography was run on a Gilson autopreparative HPLC with a diode array detector using a Xterra MS C8 19×300 mm, 7 mm as column. Purification of products were also done by flash chromatography in silica filled glass column.

List of Abbreviations

| | |
|---|---|
| Aq. | Aqueous |
| mCPBA | meta-chloroperbenzoic acid |
| Novozyme 435 ® | registered trademark name for polymer bound *candida antartica* lipase |

EXAMPLES

Synthesis of Intermediates

Example 1

Ethyl (2Z)-chloro[(3-methylphenyl)hydrazono]acetate

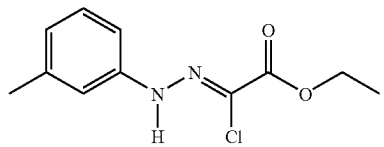

Ethyl (2Z)-chloro[(3-methylphenyl)hydrazono]acetate was synthesized as described in *Farmaco Ed. Sci.* 1985, 40(4), 259-271.

Example 2

Ethyl (2Z)-amino[3-methylphenyl)hydrazono]acetate

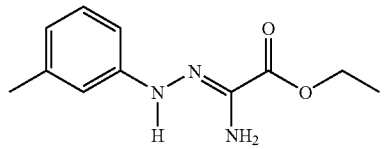

Aqueous ammonium hydroxide (20%) (768 mL) was added over 50 minutes to a stirred solution of ethyl (2Z)-chloro[(3-methylphenyl)-hydrazono]acetate (256 g, 1064 mmol) in tetrahydrofuran (1024 mL). After 40 minutes a solvent mixture of petroleum ether (250 mL) and ethyl acetate (250 mL) was added. After 15 minutes stirring the two layers were separated and the aqueous layer was extracted with ethyl acetate (2×150 mL). The combined organic layer was washed with brine (150 mL), dried over sodium sulfate, filtered and concentrated to give the title product (200 g, 85%).

$^1$H NMR (400 MHz): 7.14 (m, 1H), 6.98 (m, 1H), 6.88 (m, 1H), 6.74 (m, 1H), 6.61 (br. s, 1H), 4.38 (m, 4H), 2.32 (s, 3H), 1.39 (m, 3H).

$^{13}$C NMR (100 MHz): 162.3, 145.2, 139.1, 135.9, 129.0, 122.1, 114.8, 111.4, 62.3, 21.5, 14.2.

Example 3

Ethyl 2-(3-methylphenyl)-2H-tetrazole-5-carboxylate

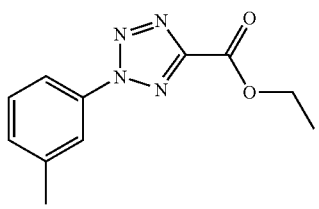

Acetic acid (207 mL, 3.62 mol) was added to a stirred solution of ethyl (2Z)-amino[3-methylphenyl)-hydrazono]acetate in tetrahydrofuran (2170 mL) and the mixture was heated to 85° C. A solution of sodium nitrite (74.8 g, 1.08 mol) in water (226 mL) was added over 3 hours. After stirring for 20 minutes the mixture was cooled to room temperature. The mixture was concentrated and to the residue was added ethyl acetate (750 mL) and aqueous saturated sodium hydrogen carbonate (500 mL). The layers were separated and the aqueous layer was extracted with ethyl acetate (250 mL). The combined organic layer was washed with brine (250 mL), dried over sodium sulfate, filtered and concentrated to give the title product (176 g, 84%).

$^1$H NMR (400 MHz): 7.99 (m, 2H), 7.44 (t, 1H), 7.34 (m, 1H), 4.56 (q, 2H), 2.45 (s, 3H), 1.48 (t, 3H).

$^{13}$C NMR (100 MHz): 157.8, 157.7, 140.2, 136.3, 131.3, 129.6, 120.8, 117.4, 62.7, 21.3, 14.2.

Example 4

1-[2-(3-Methylphenyl)-2H-tetrazol-5-yl}ethanone

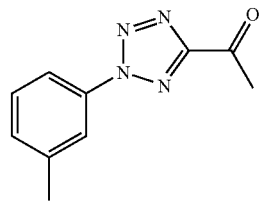

Methylmagnesium bromide (1070 mL, 1.50 mol, 1.4 M in tetrahydrofuran/toluene) in triethylamine (520 mL, 3.74 mol) was added via an addition funnel to a stirred solution of ethyl 2-(3-methylphenyl)-2H-tetrazole-5-carboxylate in dry toluene (1000 mL) at −10° C. for 5 hours. The mixture was continued to stir at −10° C. overnight. A cooled (+3° C.) solution of hydrochloric acid (37%, 500 mL) and water (500 mL) was added over 2 hours 20 minutes. The layers were separated and the organic layer was washed with water (500 mL) and brine (2×250 mL). The aqueous layer was extracted with toluene (3×500 mL) and the toluene was washed with brine (2×250 mL). The combined organic extracts were concentrated and purified on silica using dichloromethane as eluent. The concentrated product residue was triturated with petroleum ether, filtrated and dried under reduced pressure at room temperature to give the title product (90.86 g, 60%).

$^1$H NMR (400 MHz): 7.99 (m, 2H), 7.45 (t, 1H), 7.35 (m, 1H), 2.83 (m, 3H), 2.48 (s, 3H).

$^{13}$C NMR (100 MHz): 188.1, 162.6, 140.4, 136.5, 131.6, 129.8, 121.0, 117.6, 28.3, 21.5.

Example 5

1-[2-(3-Methylphenyl)-2H-tetrazol-5-yl]ethanol

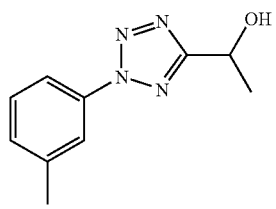

1-[2-(3-Methylphenyl)-2H-tetrazol-5-yl}ethanone (96.89 g, 479 mmol) in methanol (1000 mL) was cooled in an ice/ water bath. Sodium borohydride (29 g, 767 mmol) was added over 1 hour 30 minutes. After stirring for 40 minutes aq. acetic acid (70%, 20 mL) was added and the mixture was concentrated. Dichloromethane (400 mL) was added to the residue and was extracted with saturated aqueous sodium hydrogen carbonate (500 mL). The aqueous layer was extracted with dichloromethane (170 mL), and the combined organic layer was washed with aqueous hydrochloric acid (0.5 M, 250 mL), followed by aqueous hydrogen carbonate (280 mL), then washed with brine (500 mL), dried over sodium sulfate, filtered and concentrated to give the title product (95 g, 97%).

$^1$H NMR (400 MHz): 7.88 (m, 2H), 7.40 (t, 1H), 7.28 (m, 1H), 5.29 (m, 1H), 3.15 (m, 1H), 2.44 (s, 3H), 1.74 (m, 3H).

Example 6

(1R)-1-[2-(3-Methylphenyl)-2H-tetrazol-5-yl]ethyl acetate

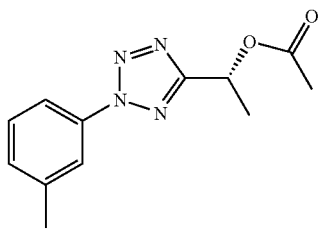

A mixture of 1-[2-(3-methylphenyl)-2H-tetrazol-5-yl] ethanol (93 g, 460 mmol) and Novozyme 435® (10 g) in dry toluene (4800 mL) was stirred slowly. Vinyl acetate (39.2 g, 460 mmol) was added and the mixture was stirred at room temperature for 5 hours. Novozyme 435® was filtrated and washed with toluene (100 mL). The filtrate was concentrated and purified on silica using petroleum ether/ethyl acetate (6:1) as eluent giving the title product (47.92 g, 42%).

$^1$H NMR (400 MHz): 7.89 (m, 2H), 7.39 (t, 1H), 7.26 (m, 1H), 6.27 (m, 1H), 2.44 (s, 3H), 2.13 (m, 3H), 1.77 (m, 3H).

Example 7

(1R)-1-[2-(3-Methylphenyl)-2H-tetrazol-5-yl]ethanol

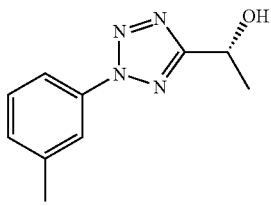

Lithium hydroxide monohydrate (16.68 g, 400 mmol) was added to a stirred solution of (1R)-1-[2-(3-methylphenyl)-2H-tetrazol-5-yl]ethyl acetate (46.6 g, 190 mmol) in tetrahydrofuran/water (1:1, 750 mL). After 3 hour reaction time the mixture was concentrated to half volume. Brine (100 mL) was added and the mixture was extracted with ethyl acetate (3×100 mL). The combined organic layer was dried over sodium sulfate, filtered and concentrated to give the title product (38.18 g, 99%).

$^1$H NMR (400 MHz): 7.89 (m, 2H), 7.42 (t, 1H), 7.28 (m, 1H), 5.29 (m, 1H), 2.72 (br. s, 1H), 2.46 (s, 3H), 1.75 (m, 3H).

$^{13}$CNMR (100 MHz): 169.3, 139.9, 136.7, 130.5, 129.4, 120.4, 117.1, 62.9, 22.3, 21.3.

Preparation of (4-methyl-5-methylthio-4H-1,2,4-triazol-3-yl)-aryls

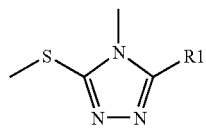

Method 1:

The corresponding aryl-carboxylic acid (n mmol) was taken up in thionyl chloride (n×1.05 mL) and refluxed for 4 h. Excess thionyl chloride was removed under reduced pressure and replaced with pyridine (n×0.52 mL). While chilled on ice bath 4-ethyl-3-thiosemicarbazide was added portion-wise (1 equivalent, rinsed/scraped in with n×0.16 mL/mmol dichloromethane). The ice bath was removed and the reaction mixture was stirred at room temperature for 24 h. The pyridine was removed under reduced pressure and replaced with aq. NaOH (1N, n×3.16 mL) and the resulting mixture was stirred at 70-80° C. for 4 hours. After cooling to room temperature, methyl iodide (1.5 eq.) in ethanol (n×0.42 mL) was added dropwise over 20 minutes. The reaction mixture was stirred at room temperature for 16 h. The product was extracted with dichloromethane (2×(n×4.2 mL)). Removal of the solvent in vacuo and flash chromatography (silica gel, 3% methanol in chloroform) yielded the title compound.

The following compounds were synthesized with method 1:

| Example | Structure | Name | Yield |
|---|---|---|---|
| 8.1 | 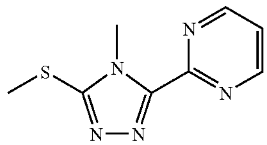 | 2-[4-methyl-5-(methylthio)-4H-1,2,4-triazol-3-yl]pyrimidine | 29% |
| GC-MS | 100% correct mass observed | | |

-continued

| Example | Structure | Name | Yield |
|---|---|---|---|
| 8.2 | 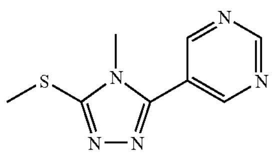 | 5-[4-methyl-5-(methylthio)-4H-1,2,4-triazol-3-yl]pyrimidine | 33% |
| GC-MS | 95% correct mass observed | | |

Method 2:

Example 8.3

2-Methyl-5-[4-methyl-5-(methylthio)-4H-1,2,4-triazol-3-yl]pyrazine

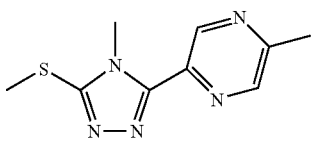

Methanol (25 mL) was added to a mixture of methyl isothiocyanate (1.052 g, 14.4 mmol) and 5-methylpyrazine-2-carbohydrazide (2.192 g, 14.4 mmol). The resulting mixture was heated at 60° C. for 1 h, and concentrated in vacuo. The residue was dissolved in aqueous sodium hydroxide solution (0.8M, 20 mL, 16 mmol) and the resulting solution was heated at 60° C. for 19 h, then cooled to room temperature. Aq. NaOH (6M, 2.6 mL, 15.6 mmol) was added followed by iodomethane (1.24 mL, 19.8 mmol) in ethanol (31 mL) plus additional water (5 mL rinse) and the resulting mixture was stirred 1 hour at room temperature. The product was partitioned between water (added 30 mL) and dichloromethane (300 mL). The aqueous layer was extracted with dichloromethane (4×100 mL). The combined organic layers were washed with water (75 mL) and brine (75 mL) and dried over sodium sulfate. Removal of the solvent in vacuo followed by flash chromatography (silica gel, 2-3% methanol in dichloromethane) yielded the title compound (2.559 g, 80%).

$^1$H NMR (300 MHz): 9.40 (s, 1H), 8.46 (s, 1H), 3.95 (s, 3H), 2.80 (s, 3H), 2.65 (s, 3H).

In a similar manner the following compound was synthesized:

| Example | Structure | Name | Yield |
|---|---|---|---|
| 8.4 | 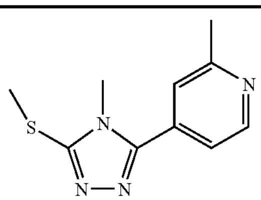 | 2-methyl-4-[4-methyl-5-(methylthio)-4H-1,2,4-triazol-3-yl]pyridine | 76% |
| $^1$H NMR | (300 MHz): 8.66 (d, 1 H), 7.49 (s, 1 H), 7.36 (d, 1 H), 3.65 (s, 3 H), 2.80 (s, 3 H), 2.65 (s, 3 H) | | |

Example 8.5

3-(4-methyl-5-methylthio-4H-1,2,4-triazol-3-yl)pyridine

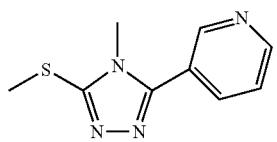

3-(4-methyl-5-methylthio-4H-1,2,4-triazol-3-yl)pyridine was synthesized as described in WO2005/080379.

Preparation of [4-methyl-5-(methylsulfonyl)-4H-1,2,4-triazol-3-yl]-aryls

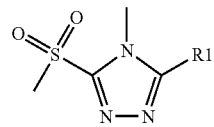

Method 1:

Meta-chloroperbenzoic acid (77%, 2.5 eq.) was added portionwise over 20 minutes to a cold solution of the corresponding (4-methyl-5-methylthio-4H-1,2,4-triazol 3-yl)-aryl (n mmol) in dichloromethane (n×6.25 mL) and the reaction mixture was stirred at room temperature for 16 hours. Saturated sodium bicarbonate (n×6.25 mL) was added and the product was extracted into dichloromethane (2×(n×12.5 mL)). Flash chromatography (silica gel, 2% methanol in chloroform) yielded the title compound.

The following compounds were synthesized with method 1:

| | | | |
|---|---|---|---|
| 9.1 | | 2-[4-methyl-5-(methylsulfonyl)-4H-1,2,4-triazol-3-yl]pyrimidine | 37% |
| GC-MS | 100% correct mass observed | | |
| ¹H NMR | (300 MHz): 8.95 (m, 2 H); 7.46 (t, 1 H); 4.38 (bs, 3 H); 3.61 (bs, 3 H) | | |
| 9.2 | | 5-[4-methyl-5-(methylsulfonyl)-4H-1,2,4-triazol-3-yl]pyrimidine | 47% |
| GC-MS | 100% correct mass observed | | |

Method 2:

Example 9.3

2-Methyl-5-[4-methyl-5-(methylsulfonyl)-4H-1,2,4-triazol-3-yl]pyrazine

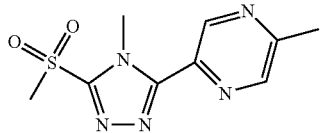

A solution of potassium permanganate (3.38 g, 17.0 mmol) in water (95 mL) was added to a solution of 2-methyl-5-[4-methyl-5-(methylthio)-4H-1,2,4-triazol-3-yl]pyrazine (1.853 g, 11.52 mmol) in glacial acetic acid (45 mL). The resulting mixture was stirred at room temperature overnight. Solid sodium hydrogen sulfate was added in portions until the dark color disappeared giving a clear colorless solution. The product was partitioned between chloroform (350 mL) and water (50 mL), and the aqueous layer was extracted with chloroform (3×150 mL). The combined organic layer was neutralized with aq. NaOH (40 is mL, 6M) and saturated sodium bicarbonate (250 mL) until gas evolution ceased and pH ~7. The organic layer was washed with brine (100 mL) and dried over sodium sulfate. Removal of the solvent in vacuo yielded the title compound (2.715 g, 93%, white solid).
¹H NMR (300 MHz): 9.44 (s, 1H), 8.55 (s, 1H), 4.36 (s, 3H), 3.62 (s, 3H), 2.69 (s, 3H).

In a similar manner the following compound was synthesized:

| Example | Structure | Name | Yield |
|---|---|---|---|
| 9.4 | 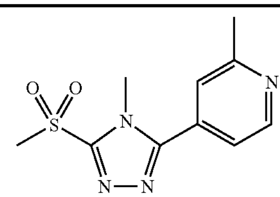 | 2-methyl-4-[4-methyl-5-(methylsulfonyl)-4H-1,2,4-triazol-3-yl]pyridine | 71% |
| ¹H NMR | (300 MHz): 8.75 (d, 1 H), 7.49 (s, 1 H), 7.37 (d, 1 H), 4.02 (s, 3 H), 3.62 (s, 3 H), 2.68 (s, 3 H) | | |

Example 9.5

3-(5-Methanesulfonyl-4-methyl-4H-1,2,4-triazol-3-yl)-pyridine 3-(5-Methanesulfonyl-4-methyl-4H-1,2,4-triazol-3-yl)-pyridine was synthesized as described in WO2005/080356

Synthesis of Final Compounds

Example 10.1

2-(4-methyl-5-{(1R)-1-[2-(3-methylphenyl)-2H-tetrazol-5-yl]ethoxy}-4H-1,2,4-triazol-3-yl)pyrimidine

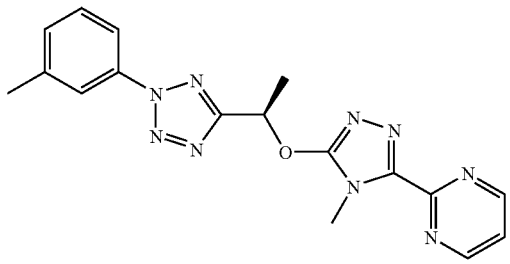

A mixture of (1R)-1-[2-(3-methylphenyl)-2H-tetrazol-5-yl]ethanol (251 mg, 1.23 mmol), 2-[4-methyl-5-(methylsulfonyl)-4H-1,2,4-triazol-3-yl]pyrimidine (239 mg, 1.00 mmol) and cesium carbonate (911 mg, 2.80 mmol) in N,N-dimethylformamide (10 mL) was stirred at 65° C. for 15 h. After cooling to room temperature, the product was partitioned between ethyl acetate (300 mL) and water (50 mL). The organic layer was washed with water (3×50 mL) and brine (50 mL), and dried over sodium sulfate. The solvent was concentrated in vacuo. Flash chromatography (silica gel, 2-3% methanol in dichloromethane) yielded the title compound (265 mg, 73%, oil).

$^1$H NMR (300 MHz): 8.85 (d, 2H); 7.93 (m, 2H); 7.42 (t, 1H); 7.29 (m, 2H); 6.68 (q, 1H); 3.88 (bs, 3H); 2.46 (bs, 3H); 2.03 (d, 3H).

LC-MS (M$^+$+1) 364.

In a similar manner the following compounds were synthesized:

| Example | Structure | Name | Yield |
|---|---|---|---|
| 10.2 | 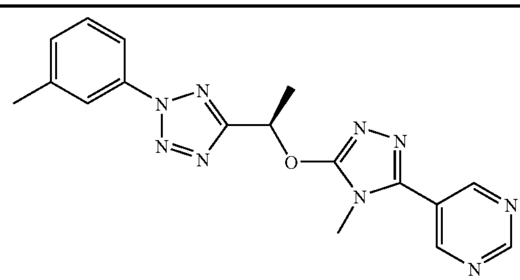 | 5-(4-methyl-5-{(1R)-1-[2-(3-methylphenyl)-2H-tetrazol-5-yl]ethoxy}-4H-1,2,4-triazol-3-yl)pyrimidine | 83% |
| $^1$H NMR | (300 MHz): 9.33 (s, 1 H), 9.09 (s, 1 H), 7.94 (m, 2 H), 7.45 (t, 1 H), 7.32 (d, 1 H), 6.61 (q, 1 H), 3.62 (s, 3 H), 2.49 (s, 3 H), 2.05 (s, 3 H) | | |
| LC-MS (M$^+$ + 1) | 364. | | |
| 10.3 | 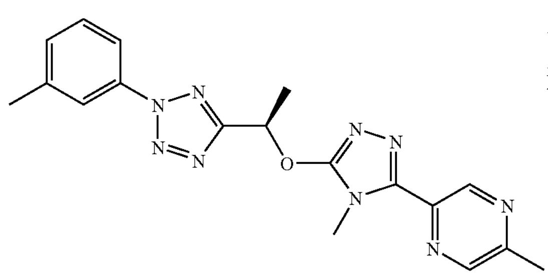 | 2-methyl-5-(4-methyl-5-{(1R)-1-[2-(3-methylphenyl)-2H-tetrazol-5-yl]ethoxy}-4H-1,2,4-triazol-3-yl)pyrazine | 100% |
| $^1$H NMR | (300 MHz): 9.36 (s, 1 H), 8.43 (s, 1 H), 7.94 (m, 2 H), 7.44 (t, 1 H), 7.32 (d, 1 H), 6.62 (q, 1 H), 3.86 (s, 3 H), 2.63 (s, 3 H), 2.48 (s, 3 H), 2.04 (d, 3 H). | | |
| LC-MS (M$^+$ + 1) | 378. | | |

| Example | Structure | Name | Yield |
|---|---|---|---|
| 10.4 | 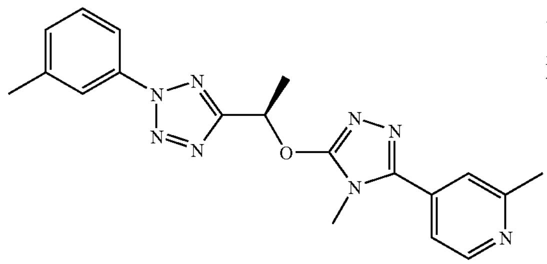 | 2-methyl-4-(4-methyl-5-{(1R)-1-[2-(3-methylphenyl)-2H-tetrazol-5-yl]ethoxy}-4H-1,2,4-triazol-3-yl)pyridine | 48% |
| $^1$H NMR | (300 MHz): 8.63 (d, 1 H), 7.93 (s + d, 2 H), 7.50 (s, 1 H), 7.44 (d, 1 H), 7.36 (d, 1 H), 7.31 (d, 1 H), 6.60 (q, 1 H), 3.60 (s, 3 H), 2.64 (s, 3 H), 2.42 (s, 3 H), 2.03 (d, 3 H) | | |
| LC-MS (M$^+$ + 1) | 377. | | |
| 10.5 | 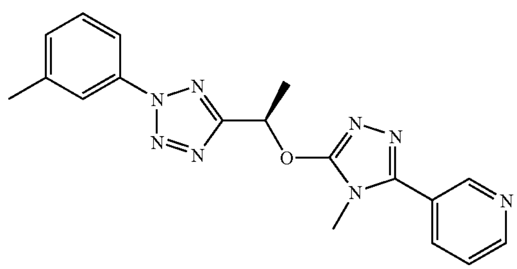 | 3-{4-Methyl-5-[(1R)-1-(2-(3-methylphenyl-2H-tetrazol-5-yl)-ethoxy]-4H-[1,2,4]triazol-3-yl}-pyridine | 83% |
| $^1$H NMR | (300 MHz): 9.33 (s, 1 H), 9.09 (s, 1 H), 7.94 (m, 2 H), 7.45 (t, 1 H), 7.32 (d, 1 H), 6.61 (q, 1 H), 3.62 (s, 3 H), 2.49 (s, 3 H), 2.05 (s, 3 H) | | |
| LC-MS (M$^+$+ 1) | 363. | | |

Biological Evaluation

Functional Assessment of mGluR5 Antagonism in Cell Lines Expressing mGluR5D

The properties of the compounds of the invention can be analyzed using standard assays for pharmacological activity. Examples of glutamate receptor assays are well known in the art as described in for example Aramori et al., *Neuron* 8:757 (1992), Tanabe et al., *Neuron* 8:169 (1992), Miller et al., *J. Neuroscience* 15: 6103 (1995), Balazs, et al., *J. Neurochemistry* 69:151 (1997). The methodology described in these publications is incorporated herein by reference. Conveniently, the compounds of the invention can be studied by means of an assay (FLIPR) that measures the mobilization of intracellular calcium, $[Ca^{2+}]_i$ in cells expressing mGluR5 or another assay (IP3) that measures inositol phosphate turnover.

FLIPR Assay

Cells expressing human mGluR5d as described in WO97/05252 are seeded at a density of 100,000 cells per well on collagen coated clear bottom 96-well plates with black sides and experiments are done 24 h following seeding. All assays are done in a buffer containing 127 mM NaCl, 5 mM KCl, 2 mM MgCl$_2$, 0.7 mM NaH$_2$PO$_4$, 2 mM CaCl$_2$, 0.422 mg/ml NaHCO$_3$, 2.4 mg/ml HEPES, 1.8 mg/ml glucose and 1 mg/ml BSA Fraction IV (pH 7.4). Cell cultures in the 96-well plates are loaded for 60 minutes in the above mentioned buffer containing 4 μM of the acetoxymethyl ester form of the fluorescent calcium indicator fluo-3 (Molecular Probes, Eugene, Oreg.) in 0.01% pluronic acid (a proprietary, non-ionic surfactant polyol —CAS Number 9003-11-6). Following the loading period the fluo-3 buffer is removed and replaced with fresh assay buffer. FLIPR experiments are done using a laser setting of 0.800 W and a 0.4 second CCD camera shutter speed with excitation and emission wavelengths of 488 nm and 562 nm, respectively. Each experiment is initiated with 160 μl of buffer present in each well of the cell plate. A 40 μl addition from the antagonist plate was followed by a 50 μL addition from the agonist plate. A 30 minute interval separates the antagonist and agonist additions. The fluorescence signal is sampled 50 times at 1 second intervals followed by 3 samples at 5 second intervals immediately after each of the two additions. Responses are measured as the difference between the peak height of the response to agonist, less the background fluorescence within the sample period. IC$_{50}$ determinations are made using a linear least squares fitting program.

IP3 Assay

An additional functional assay for mGluR5d is described in WO97/05252 and is based on phosphatidylinositol turnover. Receptor activation stimulates phospholipase C activity and leads to increased formation of inositol 1,4,5,triphosphate (IP$_3$).

GHEK stably expressing the human mGluR5d are seeded onto 24 well poly-L-lysine coated plates at 40×10$^4$ cells/well in media containing 1 μCi/well [3H] myo-inositol. Cells were incubated overnight (16 h), then washed three times and incubated for 1 h at 37° C. in HEPES buffered saline (146 mM NaCl, 4.2 mM KCl, 0.5 mM MgCl$_2$, 0.1% glucose, 20 mM HEPES, pH 7.4) supplemented with 1 unit/ml glutamate pyruvate transaminase and 2 mM pyruvate. Cells are washed once in HEPES buffered saline and pre-incubated for 10 min in HEPES buffered saline containing 10 mM LiCl. Compounds are incubated in duplicate at 37° C. for 15 min, then either glutamate (80 μM) or DHPG (30 μM) is added and incubated for an additional 30 min. The reaction is terminated by the addition of 0.5 ml perchloric acid (5%) on ice, with incubation at 4° C. for at least 30 min. Samples are collected in 15 ml polyproplylene tubes and inositol phosphates are separated using ion-exchange resin (Dowex AG1-X8 formate form, 200-400 mesh, BIORAD) columns. Inositol phosphate separation was done by first eluting glycero phosphatidyl inositol with 8 ml 30 mM ammonium formate. Next, total inositol phosphates is eluted with 8 ml 700 mM ammonium formate/100 mM formic acid and collected in scintillation vials. This eluate is then mixed with 8 ml of scintillant and [3H] inositol incorporation is determined by scintillation counting. The dpm counts from the duplicate samples are plotted and $IC_{50}$ determinations are generated using a linear least squares fitting program.

ABBREVIATIONS

BSA Bovine Serum Albumin
CCD Charge Coupled Device
CRC Concentration Response Curve
DHPG 3,5-dihydroxyphenylglycine
DPM Disintegrations per Minute
EDTA Ethylene Diamine Tetraacetic Acid
FLIPR Fluorometric Imaging Plate reader
GHEK GLAST-containing Human Embrionic Kidney
GLAST glutamate/aspartate transporter
HEPES 4-(2-hydroxyethyl)-1-piperazineethanesulfonic acid (buffer)
$IP_3$ inositol triphosphate Generally, the compounds were active in the assay above with $IC_{50}$ values less than 10 000 nM. In one aspect of the invention, the $IC_{50}$ value is less than 1 μM. In a further aspect of the invention, the $IC_{50}$ value is less than 100 nM.

| Example | $IC_{50}$/nM (IP3 assay) |
|---------|--------------------------|
| 10.1    | 36                       |
| 10.2    | 25                       |
| 10.3    | 22                       |
| 10.4    | 20                       |
| 10.5    | 23                       |

Screening for Compounds Active Against TLESR

Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 ml/kg) in a foreleg vein. Ten min after i.v. administration, a nutrient meal (10% peptone, 5% D-glucose, 5% Intralipid, pH 3.0) is infused into the stomach through the central lumen of the assembly at 100 ml/min to a final volume of 30 ml/kg. The infusion of the nutrient meal is followed by air infusion at a rate of 500 ml/min until an intragastric pressure of 10±1 mmHg is obtained. The pressure is then maintained at this level throughout the experiment using the infusion pump for further air infusion or for venting air from the stomach. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal <2s before its onset in which case the relaxation is classified as swallow-induced. The pressure difference between the LES and the stomach should be less than 2 mmHg, and the duration of the complete relaxation longer than 1 s.

The invention claimed is:

1. A compound or a pharmaceutically acceptable salt thereof, wherein the compound is
    3-{4-Methyl-5-[(1R)-1-(2-(3-methylphenyl-2H-tetrazol-5-yl)-ethoxy]-4H-[1,2,4]triazol-3-yl}-pyridine.

2. A pharmaceutical composition comprising a compound, or a pharmaceutically acceptable salt thereof, according to claim 1, as an active ingredient, together with a pharmacologically and pharmaceutically acceptable carrier.

* * * * *